(12) United States Patent
Deguchi et al.

(10) Patent No.: US 10,222,323 B2
(45) Date of Patent: Mar. 5, 2019

(54) INLINE CONCENTRATION MEASUREMENT DEVICE

(71) Applicants: TOKUSHIMA UNIVERSITY, Tokushima (JP); FUJIKIN INCORPORATED, Osaka (JP)

(72) Inventors: Yoshihiro Deguchi, Tokushima (JP); Masaaki Nagase, Osaka (JP); Nobukazu Ikeda, Osaka (JP); Michio Yamaji, Osaka (JP); Tadayuki Yakushijin, Osaka (JP)

(73) Assignees: TOKUSHIMA UNIVERSITY, Tokushima (JP); FUJIKIN INCORPORATED, Osaka (JP)

( * ) Notice: Subject to any disclaimer, the term of this patent is extended or adjusted under 35 U.S.C. 154(b) by 0 days.

(21) Appl. No.: 15/321,398

(22) PCT Filed: Jul. 23, 2015

(86) PCT No.: PCT/JP2015/003692
§ 371 (c)(1),
(2) Date: Dec. 22, 2016

(87) PCT Pub. No.: WO2016/017122
PCT Pub. Date: Feb. 4, 2016

(65) Prior Publication Data
US 2017/0199117 A1    Jul. 13, 2017

(30) Foreign Application Priority Data
Jul. 29, 2014   (JP) ................ 2014-154307

(51) Int. Cl.
*G01N 21/27*  (2006.01)
*G01N 21/05*  (2006.01)
*G01N 21/15*  (2006.01)

(52) U.S. Cl.
CPC ............ *G01N 21/27* (2013.01); *G01N 21/05* (2013.01); *G01N 21/15* (2013.01); *G01N 2021/151* (2013.01); *G01N 2201/08* (2013.01)

(58) Field of Classification Search
CPC ........ G01N 21/27; G01N 21/05; G01N 21/15; G01N 2201/08; G01N 21/0303;
(Continued)

(56) References Cited

U.S. PATENT DOCUMENTS 3,727,050 A * 4/1973 Kerr ................. G01N 21/05
                                             250/343
4,455,089 A * 6/1984 Yeung ............... G01N 21/45
                                             356/246

(Continued)

FOREIGN PATENT DOCUMENTS

EP    2239559 A4 * 11/2017
JP    H11-183366 A    7/1999
(Continued)

OTHER PUBLICATIONS

AIPN English translations of Japanese applications JP 2011127988, JP 11-183366, JP 2014102152.*
(Continued)

*Primary Examiner* — Mohamed K Amara
(74) *Attorney, Agent, or Firm* — Studebaker & Brackett PC

(57) ABSTRACT

An inline concentration measurement device comprises: a measurement cell main body with a gas flow path formed; a light incident part with a window member connected to the main body; and a light receiving part with a window member connected to the main body, wherein the gas flow path includes a gas flow path for an optical path extending straight between the window members of the light incident part and the light receiving part, a first communication part
(Continued)

making a gas inlet formed in the main body communicate with the gas flow path part for the optical path, and a second communication part making a gas outlet formed in the main body communicate with the gas flow path part for the optical path, and the first communication part obliquely extends from the gas inlet towards the window member of the light incident part.

21 Claims, 8 Drawing Sheets

(58) Field of Classification Search
CPC ....... G01N 21/3504; G01N 2021/0378; G01N 2021/058; A61B 2560/0295; A61B 2560/0456; A61B 2560/0462; G02B 6/4207; G02B 6/4209; G02B 6/4246
See application file for complete search history.

(56) References Cited

U.S. PATENT DOCUMENTS

| | | | | |
|---|---|---|---|---|
| 4,651,004 A * | 3/1987 | Uno | ................... | G01N 21/3504 250/343 |
| 5,942,755 A * | 8/1999 | Dreyer | ................... | G01J 3/108 250/339.12 |
| 7,547,904 B2 * | 6/2009 | Schmidt | ............ | B01L 3/502715 250/573 |
| 7,649,189 B2 * | 1/2010 | Cole | ................... | G01N 21/031 250/573 |
| 8,437,000 B2 * | 5/2013 | Cole | ................... | G01N 21/031 356/436 |
| 9,244,003 B1 * | 1/2016 | Matsuo | ................... | G01N 21/39 |
| 9,612,198 B2 * | 4/2017 | Colman | ................. | G01N 21/59 |
| 2002/0108437 A1 * | 8/2002 | Koch | ................... | A61B 5/0836 73/204.11 |
| 2005/0063869 A1 * | 3/2005 | Follonier | ........... | G01N 21/0303 422/82.05 |
| 2005/0286054 A1 * | 12/2005 | Chen | .................. | G01N 21/3504 356/437 |
| 2008/0106737 A1 * | 5/2008 | Weichselbaum | ....... | G01N 21/51 356/341 |
| 2008/0151248 A1 * | 6/2008 | Cole | ......................... | G01J 3/02 356/437 |
| 2010/0214556 A1 * | 8/2010 | Mannhardt | ........... | G01N 21/15 356/73 |
| 2013/0166242 A1 * | 6/2013 | Ido | ................... | G01N 35/00693 702/104 |
| 2014/0063494 A1 * | 3/2014 | Hatahori | ............... | G01N 21/05 356/246 |
| 2014/0268157 A1 * | 9/2014 | Bogoev | ............. | G01N 21/3504 356/437 |
| 2014/0291526 A1 * | 10/2014 | Killich | ................... | G01N 21/39 250/343 |

FOREIGN PATENT DOCUMENTS

| | | |
|---|---|---|
| JP | 2000-206045 A | 7/2000 |
| JP | 2004-198121 A | 7/2004 |
| JP | 2011-127988 A | 6/2011 |
| JP | 2012-137429 A | 7/2012 |
| JP | 2014-102152 A | 6/2014 |
| WO | 1999/034192 A1 | 7/1999 |
| WO | WO-2009060169 A1 * | 5/2009 ............... F25C 1/00 |

OTHER PUBLICATIONS

International Search Report issued in PCT/JP2015/003692; dated Oct. 13, 2015.

* cited by examiner

INLINE CONCENTRATION MEASUREMENT DEVICE

TECHNICAL FIELD

The present invention relates to an inline concentration measurement device incorporated in a supply line of a raw material fluid of an organic metal (MO) gas or the like to a semiconductor manufacturing equipment for measuring gas concentration in the gas supply line based on a principal of an absorptiometric method.

BACKGROUND ART

An inline concentration measurement device to be incorporated in a raw material fluid supply line of a semiconductor manufacturing equipment is conventionally known (for example, Patent Document 1).

FIG. 8 is a schematic diagram showing a configuration of an embodiment of a related concentration measurement device. In FIG. 8, light having a prescribed wavelength emitted from a light source 1 including a light emitting diode is transmitted to a light incident part 3 through an optical fiber 2, then entered to a gas flow path 5 through a window member 4 made of quartz glass, sapphire glass or the like equipped in the light incident part 3 to be absorbed by gas in the gas flow path 5, and finally received by a light receiving part 8 including a photo diode 7 through an opposing window member 6. The photo diode 7 converts the detected light into an electrical signal and outputs, then the outputted signal is sent to a control computation unit 10 including a CPU through an electric wiring 9, and gas concentration is finally displayed on a displaying part 11 after a certain computing process by the control computation unit 10 is conducted. The control computation unit 10 also controls a power source 12 for supplying power to the light source 1. The light source 1 is capable of emitting the light having one wavelength or two wavelengths or more.

As shown in a detailed cross section view of FIG. 9, the gas flow path 5 shown in FIG. 8 includes a metal measurement cell main body 15 with the gas flow path 5 formed, the light incident part 3 connected to the measurement cell main body 15 through a gasket 16, and the light receiving part 8 connected to the measurement cell main body 15 through a gasket 17. The gas flow path 5 includes a gas flow path part 5a for an optical path extending straight through between the light incident part 3 and the light receiving part 8 to provide an optical path L and a left-and-fight pair of communication parts 5b and 5c that communicate with the gas flow path part 5a for the optical path and open on a bottom face 15a of the measurement cell main body 15. The light incident part 3 is equipped with the window member 4 and the optical fiber 2. The light receiving part 8 is equipped with the window member 6 and the photo diode 7. A joint 20 at a gas inlet side and a joint 21 at a gas outlet side are connected to the bottom face 15a of the measurement cell main body 15.

CITATION LIST

Patent Literature

Patent Document 1: Japanese Laid-Open Patent Publication No. 2000-206045

SUMMARY OF INVENTION

Technical Problem

An inline concentration measurement device having a configuration shown in FIG. 9 has a problem that window members 4 and 6 are required to be frequently changed due to accumulation of an organic metal material on the window members 4 and 6 caused by a MO gas flow.

Solution to Problem

For example in a case of a window member 4, as shown in an enlarged view of FIG. 10, the present inventors found through extensive research that a dead space D near the window member 4 where gas tends to retain lets an organic metal material accumulate on the window member 4 as the MO gas flows. The same applies to a window member 6 (FIG. 9).

To solve the above described problem, an inline concentration measurement device according to a first aspect of the present invention includes a measurement cell main body with a gas flow path formed, a light incident part with a window member connected to the measurement cell main body, and a light receiving part with a window member connected to the measurement cell main body, and the gas flow path includes a gas flow path part for an optical path extending straight between the window member of the light incident part and the window member of the light receiving part to provide the optical path, a first communication part making a gas inlet formed in the measurement cell main body communicate with the gas flow path part for the optical path, and a second communication part making a gas outlet formed in the measurement cell main body communicate with the gas flow path part for the optical path where the first communication part obliquely extends from the gas inlet towards the window member of the light incident part.

In an inline concentration measurement device according to a second aspect of the present invention, in the first aspect, the second communication part obliquely extends from the gas outlet towards the window member of the light receiving part.

An inline concentration measurement device according to a third aspect of the present invention includes a measurement cell main body with a gas flow path formed, a light incident part with a window member connected to the measurement cell main body, and a light receiving part with a window member connected to the measurement cell main body, and the gas flow path includes a gas flow path part for an optical path extending straight between the window member of the light incident part and the window member of the light receiving part to provide the optical path, a first communication part making a gas inlet formed in the measurement cell main body communicate with the gas flow path part for the optical path, and a second communication part making a gas outlet formed in the measurement cell main body communicate with the gas flow path part for the optical path where the second communication part obliquely extends from the gas outlet towards the window member of the light receiving part.

In an inline concentration measurement device according to a fourth aspect of the present invention, in the first or third aspect, a cross section area of the flow path of the first communication part is smaller than a cross section area of the gas flow path part for the optical path.

In an inline concentration measurement device according to a fifth aspect of the present invention, in the first or third aspect, the light incident part includes a holding body for holding an optical fiber and clamping the window member between the measurement cell main body and the holding body, and a fitting recessed part is formed either on the measurement cell main body or the holding body and a fitting projected part which fits the fitting recessed part is formed on the other with the window member held between a recess bottom face of the fitting recessed part and a protruded end face of the fitting projected part.

In an inline concentration measurement device according to a sixth aspect of the present invention, in the fifth aspect, the fitting recessed part is formed as a stepped recess and the fitting projected part is formed as a stepped projection that fits the stepped recess with a sealing face formed as an abutting face by the stepped part of the fitting recessed part and the stepped part of the fitting projected part abutting each other.

In an inline concentration measurement device according to a seventh aspect of the present invention, in the first or third aspect, the light receiving part includes a holding body for holding a photo diode and clamping the window member between the measurement cell main body and the holding body, and a fitting recessed part is formed either on the measurement cell main body or the holding body and a fitting projected part which fits the fitting recessed part is formed on the other with the window member held between a recess bottom face of the fitting recessed part and a protruded end face of the fitting projected part.

In an inline concentration measurement device according to an eighth aspect of the present invention, in the seventh aspect, the fitting recessed part is formed as a stepped recess and the fitting projected part is formed as a stepped projection that fits the stepped recess with a sealing face formed as an abutting face by the stepped part of the fitting recessed part and the stepped part of the fitting projected part abutting each other.

In an inline concentration measurement device according to a ninth aspect of the present invention, in the first or third aspect, the light incident part includes a collimator lens for collimating incident light entering to the gas flog path part for the optical path.

In an inline concentration measurement device according to a tenth aspect of the present invention, in the first or third aspect, the window members are configured to obliquely cross the optical path of the gas flow path part for the optical path.

In an inline concentration measurement device according to an eleventh aspect of the present invention, in the first or third aspect, a gas inflow path communicating with the first communication part for sending gas is provided and a cross section area of the gas inflow path is larger than a cross section area of the flow path of the first communication part.

Advantageous Effects of Invention

According to the present invention, a first communication part making a gas inlet formed in a measurement cell main body to communicate with a gas flow path part for an optical path is configured to obliquely extend from the gas inlet towards a window member of a light incident part to eliminate retention of gas near the window member by causing a flow of the gas on a surface of the window member for reducing undesired accumulation of a raw material on the surface of the window member in the light incident part.

A second communication part is also configured to obliquely extend from a gas outlet towards a window member of a light receiving part for reducing undesired accumulation of the raw material on the window member of the light receiving part.

In addition, a cross section area of a flow path of the first communication part is configured to be smaller than a cross section area of the gas flow path part for the optical path to make speed of a flow in the first communication part faster than the flow in the gas flow path part for the optical path for reducing the accumulation of an organic metal material or the like in the light incident part.

DESCRIPTION OF EMBODIMENTS

Figure 1:
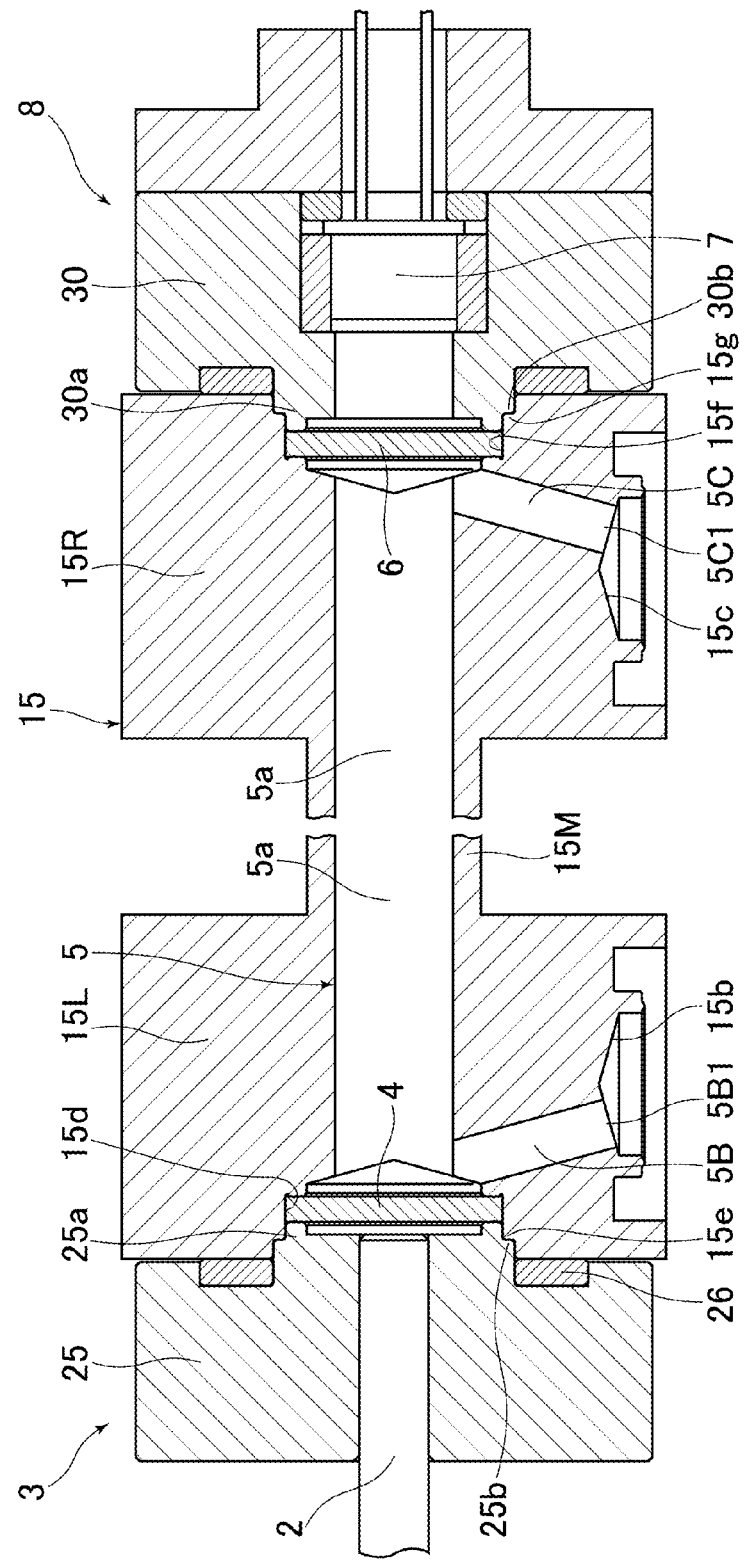
FIG. 1 A sectional view of an essential part of an inline concentration measurement device according to a first embodiment of the present invention.

Hereinafter, embodiments of an inline concentration measurement device according to the present invention are described with reference to drawings, wherein like reference numerals designate corresponding or identical elements throughout all drawings and embodiments including the background arts, and some duplicated explanations are emitted in the following description.

FIG. 1 illustrates an inline concentration measurement device according to a first embodiment of the present invention. The inline concentration measurement device of the first embodiment includes a measurement cell main body 15 with a gas flow path 5 formed, a light incident part 3 with a window member 4 connected to the measurement cell main body 15, and a light receiving part 8 with a window member 6 connected to the measurement cell main body 15. The gas flow path 5 includes a gas flow path part 5*a* for an optical path linearly formed between the window member 4 of the light incident part 3 and the window member 6 of the light receiving part 8 to provide the optical path, a first communication part 5B making a gas inlet 5B1 communicate with the gas flow path part 5*a* for the optical path formed in the measurement cell main body 15, and a second communication part 5C making a gas outlet 5C1 communicate with the gas flow path part 5*a* for the optical path formed in the measurement cell main body 15. The first communication part 5B obliquely extends from the gas inlet 5B1 towards the window member 4 of the light incident part 3.

Figure 7:
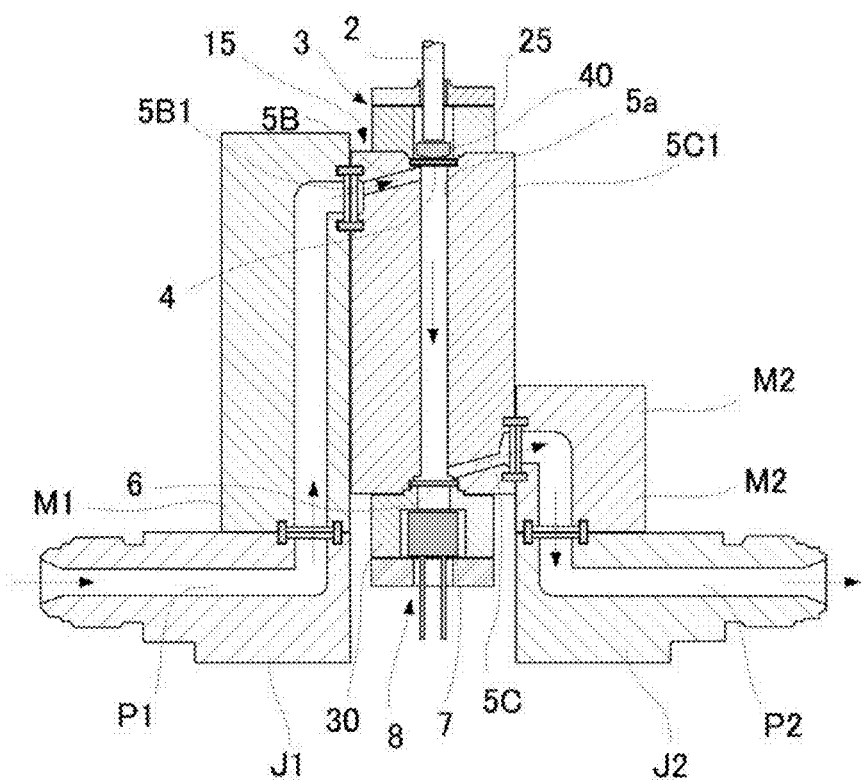
FIG. 7 A sectional view of an inline concentration measurement device according to a sixth embodiment of the present invention.
Figure 8:
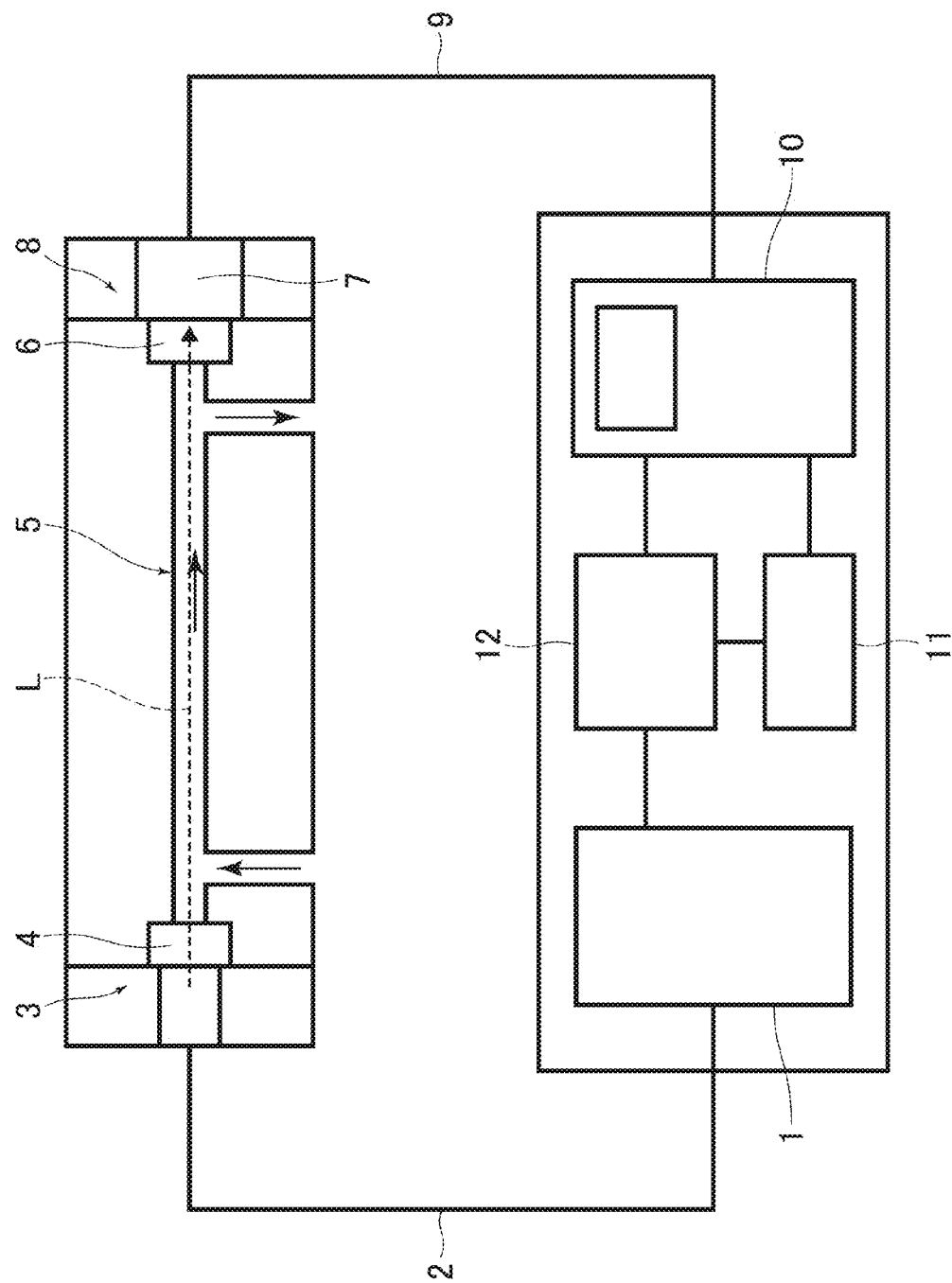
FIG. 8 A schematic diagram illustrating a basic configuration of a related concentration measurement device.
Figure 9:
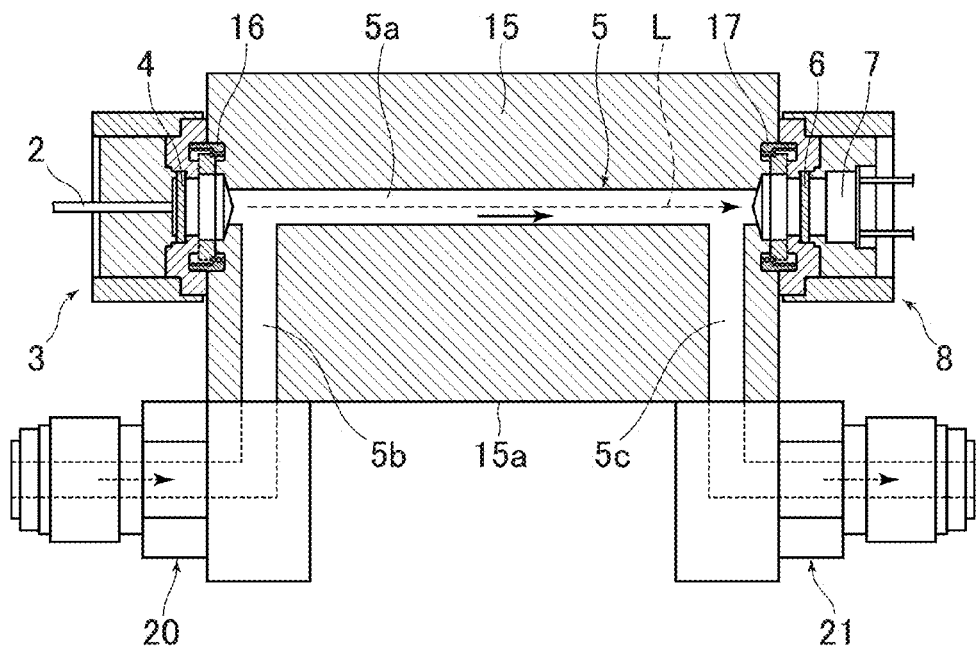
FIG. 9 A sectional view of an essential part of a related inline concentration measurement device.
Figure 10:
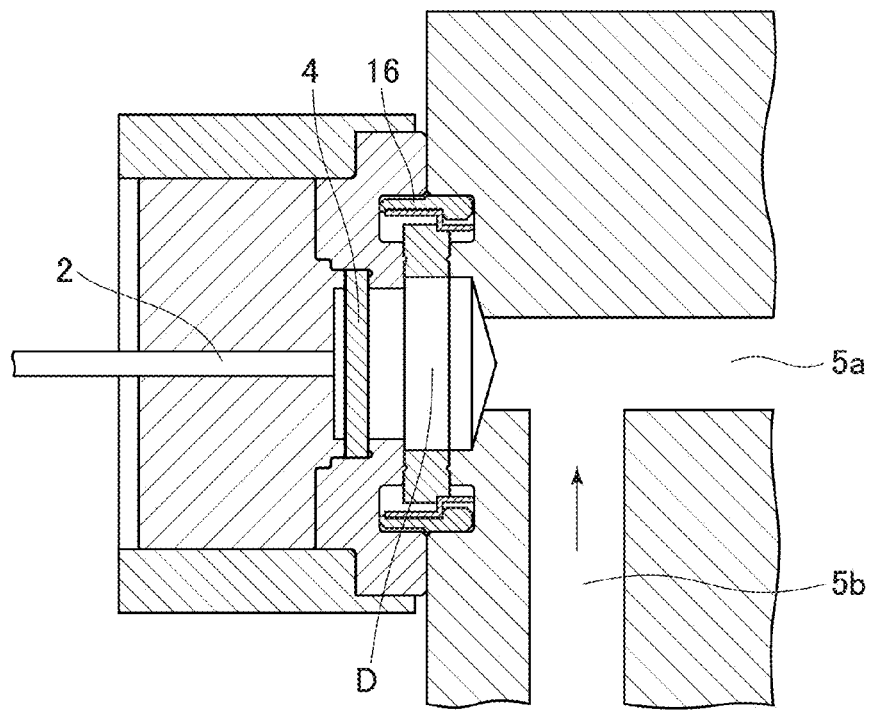
FIG. 10 An enlarged sectional view of a part of FIG. 9.

In the embodiment illustrated in FIG. 1, the measurement cell main body 15 includes right and left block bodies 151, and 15R and a pipe body 15M connecting the right and left block bodies 15L and 15R. The pipe body 15M has a continuous cylindrical shape though the middle part thereof is not shown in FIG. 1. The measurement cell main body may be various shapes and can be, for example as shown in FIG. 7, a rectangular parallelepiped shape instead of the cylindrical pipe shape.

The gas inlet 5B1 and the gas outlet 5C1 respectively open to recessed parts 15b and 15c formed on a surface (a bottom face in the shown embodiment) of the measurement cell main body 15. Joints J1 and J2 are respectively connected to the recessed parts 15b and 15c through gaskets (see FIGS. 2 and 3).

The second communication part 5C obliquely extends from the gas outlet 5C1 towards the window member 6 of the light receiving part 8.

A cross section area of a flow path of the first communication part 5B is formed to be smaller than a cross section area of the gas flow path part 5a for the optical path and more preferably, the cross section area of the flow path of the first communication part 5B is formed to be no more than a half of the cross section area of the gas flow path part for the optical path.

The light incident part 3 includes a holding body 25 holding an optical fiber 2 and clamping the window member 4 facing to the gas flow path 5 between the measurement cell main body 15 and the holding body. A fitting recessed part 15d is formed on the measurement cell main body 15 and a fitting projected part 25a which fits the fitting recessed part 15d is formed on the holding body 25. The window member 4 is clamped between a recess bottom face of the fitting recessed part 15d and a protruded end face of the fitting projected part 25a of the holding body 25.

Sapphire glass plates may be preferably used for the window members 4 and 6. A gasket 26 intervenes between the holding body 25 and the measurement cell main body 15. The first communication part 5B opens on the window member 4 to communicate with the gas flow path part 5a for the optical path.

The fitting recessed part 15d is formed as a stepped recess with a stepped part 15e and the fitting projected part 25a is formed as a stepped projection with a stepped part 25b that fits the stepped recessed part 15d. An abutting face by the stepped part 15e of the fitting recessed part 15d and the stepped part 25b of the fitting projected part 25a abutting each other forms a sealing face.

The light receiving part 8 includes the window member 6 facing the gas flow path 5, a photo diode 7, and a holding body 30 holding the photo diode 7 and clamping the window member 6 between the measurement cell main body 15 and the holding body, and a fitting recessed part 15f is formed on the measurement cell main body 15 and a fitting projected part 30a which fits the fitting recessed part 15f is formed on the holding body 30. The window member 6 is clamped between a recess bottom face of the fitting recessed part 15f and a protruded end face of the fitting projected part 30a.

The fitting recessed part 15f is formed as a stepped recess with a stepped part 15g and the fitting projected part 30a is formed as a stepped projection with a stepped part 30b that fits the stepped recessed part 15f with the stepped part 15g. An abutting face by the stepped part 15g of the fitting recessed part 15f and the stepped part 30b of the fitting projected part 30a abutting each other forms a sealing face.

Figure 2:
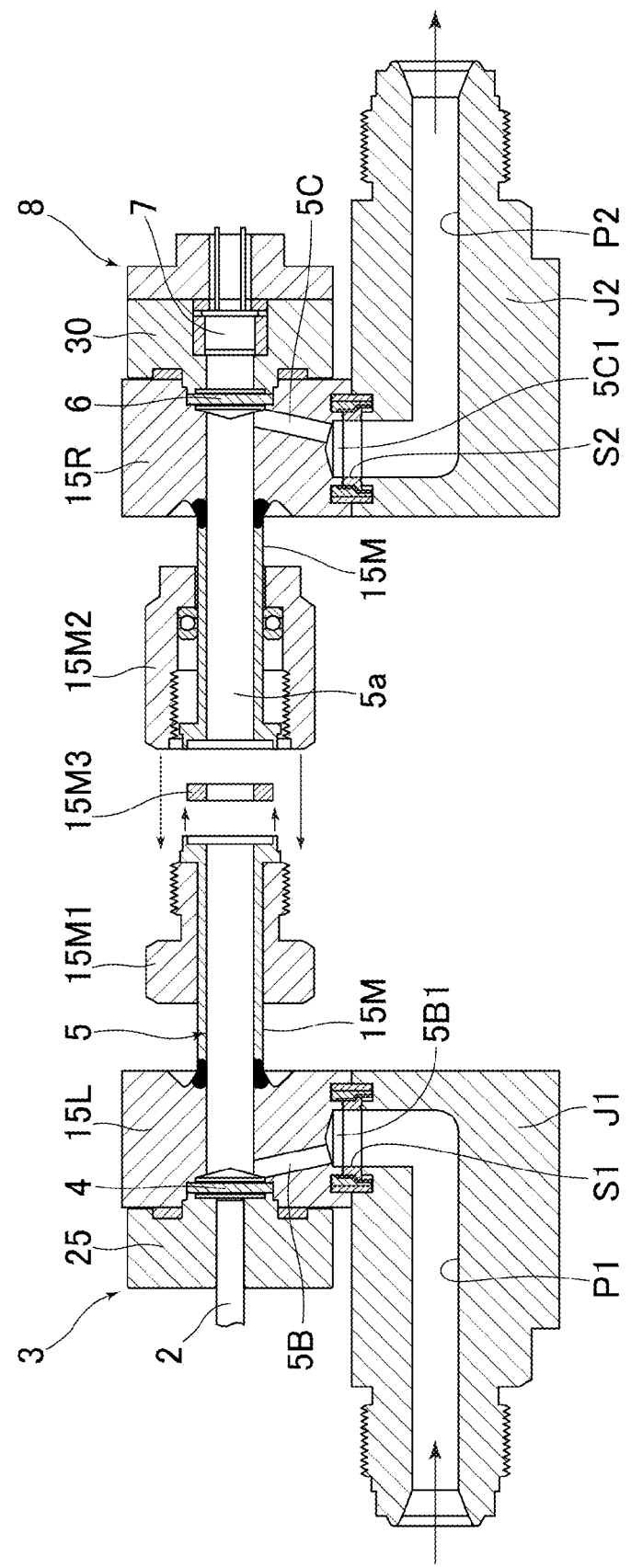
FIG. 2 A sectional view of an inline concentration measurement device without a coupling according to a second embodiment of the present invention.
Figure 3:
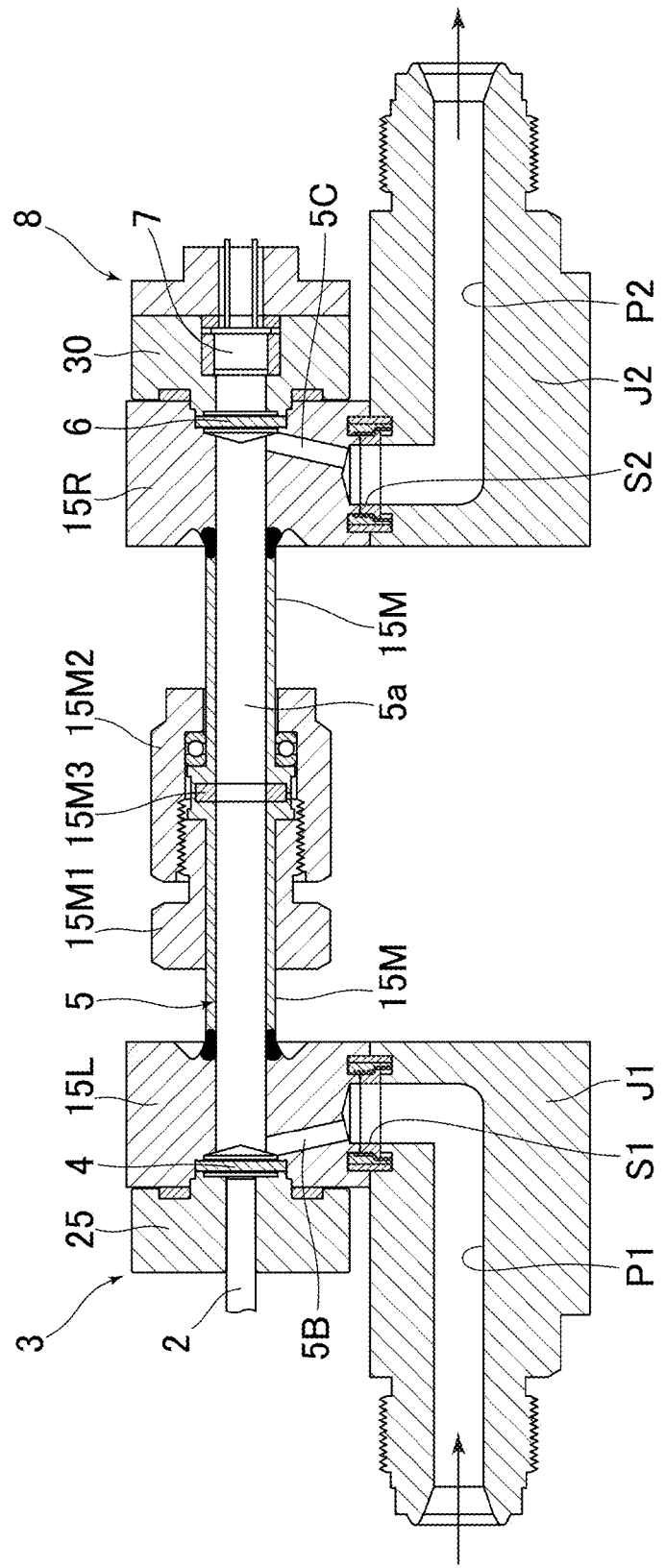
FIG. 3 A sectional view of the inline concentration measurement device illustrated in FIG. 2 with the coupling being coupled.

FIGS. 2 and 3 illustrate an inline concentration measurement device according to a second ea embodiment of the present invention. In the inline concentration measurement device according to the second embodiment, pipe bodies 15M respectively formed with gas flow path parts 5a for an optical path are detachably connected in a middle section with male and female couplings 15M1 and 15M2. A reference sign 15M3 designates a gasket for sealing. Joints J1 and J2 are respectively connected to a gas inlet 5B1 and a gas outlet 5C1 for connection with pipelines (not shown) through sealing gaskets S1 and S2. A gas inflow path P1 is formed in the joint J1. The gas inflow path P1 communicates with a first communication path 5B. A cross section area of the gas inflow path P1 is larger than a cross section area of the first communication path 5B. Thus flow speed of gas that has flown through the gas inflow path P1 increases while the gas passes through the first communication path 5B. A gas outflow path P2 is formed in the joint J2.

Figure 4:
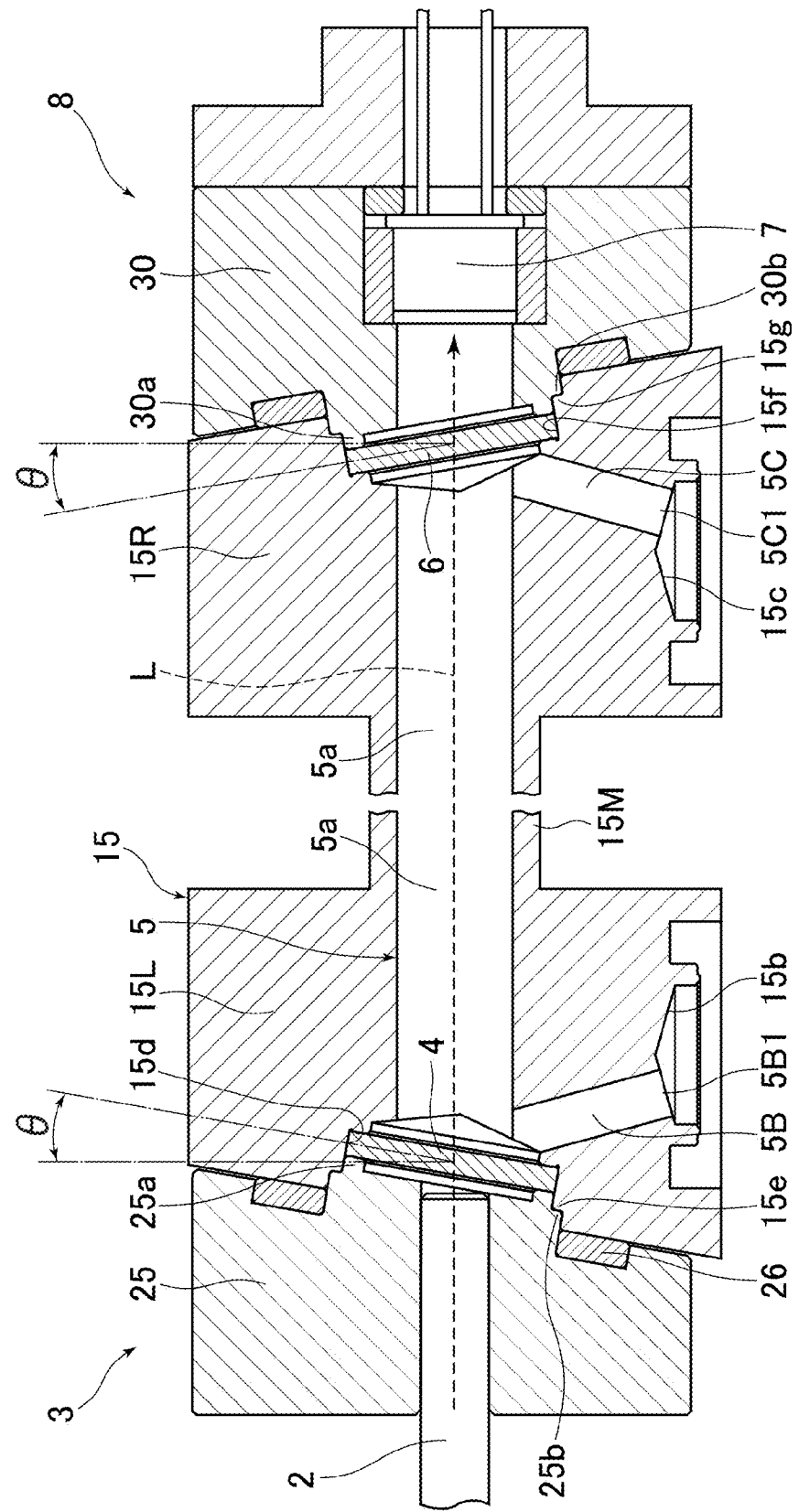
FIG. 4 A sectional view of an inline concentration measurement device according to a third embodiment of the present invention.

FIG. 4 illustrates an inline concentration measurement device according to a third embodiment of the present invention. In the cases of the first and second embodiments, the window members 4 and 6 are orthogonal to the optical path, however window members 4 and 6 are configured to obliquely cross an optical path L in the inline concentration measurement device of the third embodiment. Here, faces where holding bodies 15L and 15R are attached are obliquely formed on a measurement cell main body 15 to achieve the above configuration. An inclination angle θ of the window members 4 and 6 relative to a plane orthogonal to the optical path L may be, for example, 10° to 45°. Measurement error affected by reflection of light on the window members 4 and 6 may be reduced by inclining the window members 4 and 6 relative to the optical path L.

Figure 5:
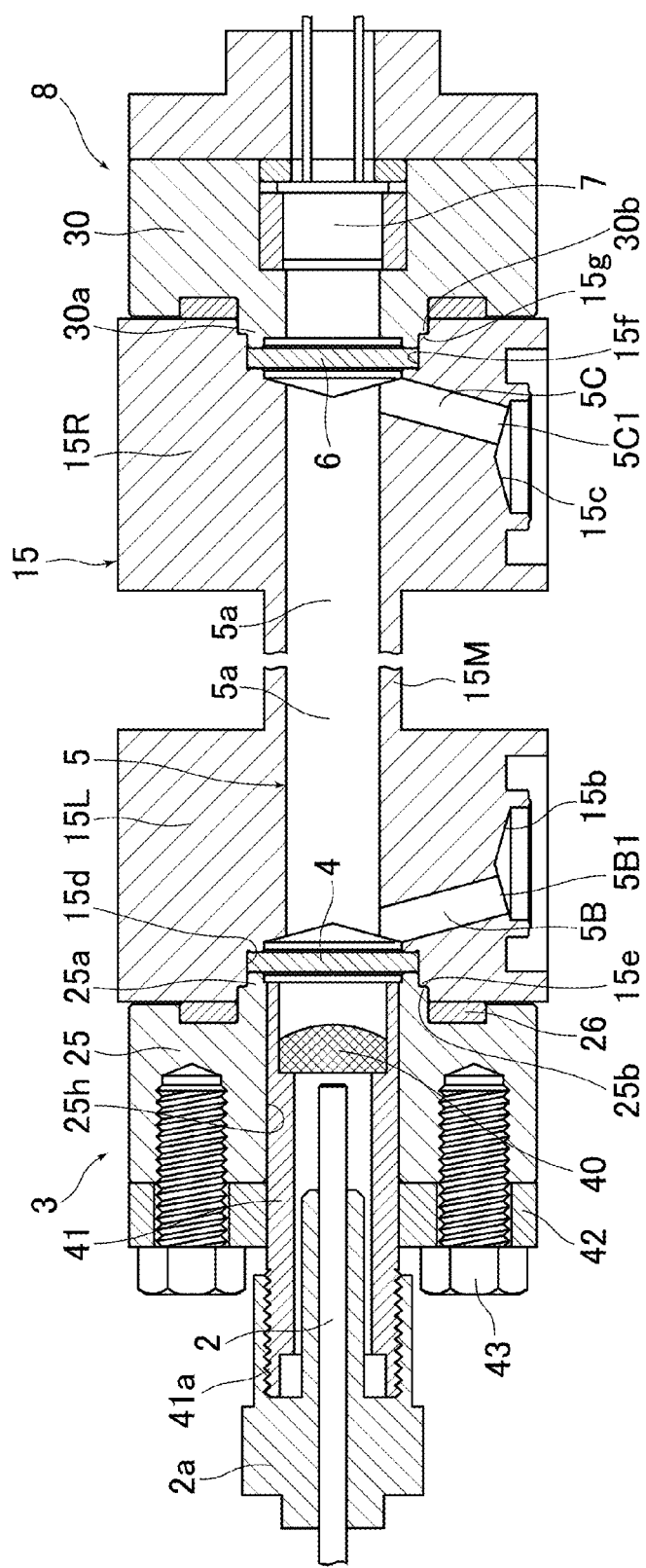
FIG. 5 A sectional view of an inline concentration measurement device according to a fourth embodiment of the present invention.

FIG. 5 illustrates an inline concentration measurement device according to a fourth embodiment of the present invention. In the inline concentration measurement device according to the fourth embodiment, a light incident part 3 includes a collimator lens 40 for collimating incident light entering to a gas flow path part 5a for an optical path. The collimator lens 40 can be provided behind a window member 4, in other words, in an opposite side of the gas flow path part 5a for the optical path with the window member 4 in between. Measurement accuracy may be improved by collimating the incident light entering to the gas flow path part 5a for the optical path with the collimator 40 to increase the amount of light in a cell. In the embodiment shown, the collimator lens 40 is stored and fixed in a cylindrical body 41. The cylindrical body 41 is inserted to a hole 25h of a holding body 25 and a flange 42 welded to the cylindrical body 41 is fixed to the holding body 25 with a bolt 43. A connector 2a holding an optical fiber 2 is connected to a threaded part 41a formed on a rear outer peripheral surface of the cylindrical body 41.

Figure 6:
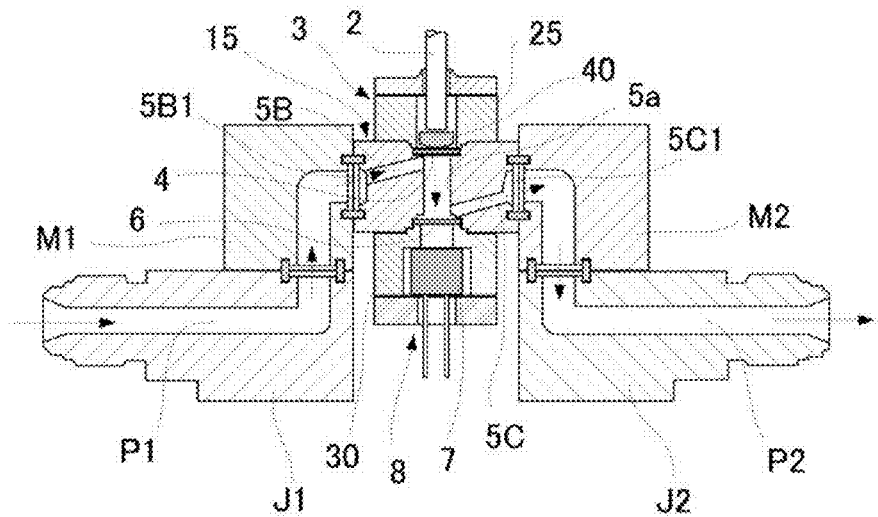
FIG. 6 A sectional view of an inline concentration measurement device according to a fifth embodiment of the present invention.

FIGS. 6 and 7 respectively illustrate inline concentration measurement devices according to fifth and sixth embodiments of the present invention. The both inline concentration measurement devices of the fifth and sixth embodiments are vertical type which has a gas flow path part 5a for an optical path arranged in a height direction. In the sixth embodiment shown in FIG. 7, the gas flow path part 5a for the optical path is longer than the gas flow path part 5a for the optical path in the fifth embodiment shown in FIG. 6. In the both fifth and sixth embodiments, a measurement cell main body 15 is formed as a block body. The gas flow path part 5a for the optical path vertically penetrates a center part of the measurement cell main body 15. A gas inlet 5B1 is formed on one side and a gas outlet SCI is formed on another side of the measurement cell main body 15. A first communication part 5B makes the gas inlet 5B1 communicate with the gas flow path part 5a for the optical path. The first communication part 5B obliquely extends towards a window member 4 of a light incident part 3. A second communication part 5C makes the gas flow path part 5a for the optical path communicate with the gas outlet 5C1. The second communication part 5C obliquely extends from the gas outlet 5C1 towards a window member 6 of a light receiving part 8. Cross section areas of flow paths in the first communication part 5B and the second communication part 5C are formed to be smaller than a cross section area of the gas flow path part 5a for the optical path. Middle blocks M1 and M2 respectively connect to right and left sides of the measurement cell main body 15 with joints J1 and J2 respectively attached to the middle blocks M1 and M2. A gas inflow path P1 penetrating through the middle block M1 as well as the joint J1 communicates with the first communication part 5B. A gas outflow path P2 penetrating through the middle block M2 as well as the joint J2 communicates with the second communication part 5C. A cross section area of the gas inflow path P1 is formed to be larger than the cross section area of the first communication path 5B. Thus flow speed of the gas that has flown through the gas inflow path P1 increases while the gas passes through the first communication path 5B. A ground contact area of such the vertical type inline concentration measurement device may be smaller than a ground contact area of the horizontal type device such as the ones according to the first to fourth embodiments.

In the inline concentration measurement device having the above configuration, the first communication part 5B making the gas inlet 5B1 formed in the measurement cell main body 15 communicate with the gas flow path part 5a for the optical path is configured to obliquely extend from the gas inlet 5B1 towards the window member 4 of the light incident part 3 to eliminate retention of the gas near the window member 4 by making a flow of the gas flowing from the first communication part 5B towards a surface of the window member 4 for reducing undesired accumulation of an organic metal material or the like on the surface of the window member 4.

In addition, the accumulation of the organic metal material or the like on the window member 4 of the light incident part 3 may be reduced by configuring the cross section area of the flow path of the first communication part 5B to be smaller than the cross section area of the gas flow path part 5a for the optical path to make speed of the flow in the gas flow path part 5a for the optical path faster than the flow in the first communication part 5B.

Also, the accumulation of the organic metal material or the like on the window member 4 of the light incident part 3 may be reduced by making the cross section area of the flow path of the first communication part 5B smaller than the cross section area of the gas inflow path P1 sending the gas to the first communication part 5B to increase the speed of the flow in the first communication part 5B.

The present invention is not limited to the above described embodiments but variations may be made within the scope of the invention. For example, in the previously described embodiments, the fitting recess is made on the measurement cell main body and the fitting projection is made on the holding body. On the contrary, however, the fitting projection may be made on the measurement cell main body and the fitting recess may be made on the holding body.

REFERENCE SIGNS LIST 2 optical fiber
3 light incident part
4 window member
5 gas flow path
5a gas flow path part for the optical path
5B first communication path
5B1 gas inlet
5C second communication path
5C1 gas outlet
6 window member
7 photo diode
8 light receiving part
15 measurement cell main body
15d fitting recessed part
15e stepped part
15f fitting recessed part
15g stepped part
25 holding body
25a fitting projected part
25b stepped part
30 holding body
30a fitting projected part
30b stepped part
P1 gas inlet path

The invention claimed is:

1. An inline concentration measurement device, comprising:
a measurement cell main body in which a gas flow path is formed;
a light incident part having a window member and being connected to the measurement cell main body; and
a light receiving part having a window member and being connected to the measurement cell main body, wherein
the gas flow path includes a gas flow path part for an optical path including a first end and a second end extending straight between the window member of the light incident part at the first end and the window member of the light receiving part to provide the optical path at the second end, a first communication part making a gas inlet formed in the measurement cell main body communicate with the gas flow path part for the optical path, and a second communication part making a gas outlet formed in the measurement cell main body communicate with the gas flow path part for the optical path,
the first communication part extends straight from a first point at the gas inlet toward a second point at the first end of the gas flow path part for an optical path, the first point nearer than the second point to a plane perpendicular to a center of the gas flow path part for an optical path,
the first communication part obliquely extends from the gas inlet towards a surface of the window member of the light incident part, and
the first communication part is connected to the gas flow path part for an optical path at an acute angle with respect to a longitudinal axis of the gas flow path part for an optical path to form the gas flow path bending at the acute angle, and a connection portion of the first communication part and the gas flow path part for the optical path is located in a vicinity of the window member of the light incident part.

2. The inline concentration measurement device of claim 1, wherein
the second communication part obliquely extends from the gas outlet towards the window member of the light receiving part.

3. The inline concentration measurement device of claim 1, wherein
a cross section area of a flow path in the first communication part is smaller than a cross section area of the gas flow path part for the optical path.

4. The inline concentration measurement device of claim 1, wherein
the light incident part includes a holding body for holding an optical fiber and clamping the window member between the measurement cell main body and the holding body, and
a fitting recessed part is formed either on the measurement cell main body or the holding body and a fitting projected part which fits the fitting recessed part is formed on the other with the window member held between a recess bottom face of the fitting recessed part and a protruded end face of the fitting projected part.

5. The inline concentration measurement device of claim 4, wherein
the fitting recessed part is formed as a stepped recess and the fitting projected part is formed as a stepped projection that fits the stepped recess with a sealing face formed as an abutting face by a stepped part of the fitting recessed part and a stepped part of the fitting projected part abutting each other.

6. The inline concentration measurement device of claim 1, wherein
the light receiving part includes a holding body for holding a photo diode and clamping the window member between the measurement cell main body and the holding body, and
a fitting recessed part is formed either on the measurement cell main body or the holding body and a fitting projected part which fits the fitting recessed part is formed on the other with the window member held between a recess bottom face of the fitting recessed part and a protruded end face of the fitting projected part.

7. The inline concentration measurement device of claim 6, wherein
the fitting recessed part is formed as a stepped recess and the fitting projected part is formed as a stepped projection that fits the stepped recess with a sealing face formed as an abutting face by a stepped part of the fitting recessed part and a stepped part of the fitting projected part abutting each other.

8. The inline concentration measurement device of claim 1, wherein
the light incident part includes a collimator lens for collimating incident light entering to the gas flow path part for the optical path.

9. The inline concentration measurement device of claim 1, wherein
the window members are configured to obliquely cross the optical path of the gas flow path part for the optical path.

10. The inline concentration measurement device of claim 1, wherein
a gas inflow path communicating with the first communication part for sending gas thereto is provided and a cross section area of the gas inflow path is larger than a cross section area of the flow path in the first communication part.

11. The inline concentration measurement device of claim 1, wherein
the measurement cell main body includes a block body, an end portion of which is configured to support the window member of the light incident part, and
the first communication part is formed in the block body.

12. An inline concentration measurement device, comprising:
a measurement cell main body in which a gas flow path is formed;
a light incident part having a window member and being connected to the measurement cell main body; and
a light receiving part having a window member and being connected to the measurement cell main body, wherein
the gas flow path includes a gas flow path part for an optical path including a first end and a second end extending straight between the window member of the light incident part at the first end and the window member of the light receiving part at the second end to provide the optical path, a first communication part making a gas inlet formed in the measurement cell main body communicate with the gas flow path part for the optical path, and a second communication part making a gas outlet formed in the measurement cell main body communicate with the gas flow path part for the optical path,
the first communication part extends straight from a first point at the gas inlet toward a second point at the first end of the gas flow path part for an optical path, the first point nearer than the second point to a plane perpendicular to a center of the gas flow path part for an optical path,
the second communication part obliquely extends from the gas outlet towards a surface of the window member of the light receiving part, and
the second communication part is connected to the gas flow path part for an optical path at an acute angle with respect to a longitudinal axis of the gas flow path part for an optical path to form the gas flow path bending at the acute angle, and a connection portion of the second communication part and the gas flow path part for the optical path is located in a vicinity of the window member of the light receiving part.

13. The inline concentration measurement device of claim 12, wherein
a cross section area of a flow path in the first communication part is smaller than a cross section area of the gas flow path part for the optical path.

14. The inline concentration measurement device of claim 12, wherein
the light incident part includes a holding body for holding an optical fiber and clamping the window member between the measurement cell main body and the holding body, and
a fitting recessed part is formed either on the measurement cell main body or the holding body and a fitting projected part which fits the fitting recessed part is formed on the other with the window member held between a recess bottom face of the fitting recessed part and a protruded end face of the fitting projected part.

15. The inline concentration measurement device of claim 14, wherein
the fitting recessed part is formed as a stepped recess and the fitting projected part is formed as a stepped projection that fits the stepped recess with a sealing face formed as an abutting face by a stepped part of the fitting recessed part and a stepped part of the fitting projected part abutting each other.

16. The inline concentration measurement device of claim 12, wherein
the light receiving part includes a holding body for holding a photo diode and clamping the window member between the measurement cell main body and the holding body, and
a fitting recessed part is formed either on the measurement cell main body or the holding body and a fitting projected part which fits the fitting recessed part is formed on the other with the window member held between a recess bottom face of the fitting recessed part and a protruded end face of the fitting projected part.

17. The inline concentration measurement device of claim 16, wherein
the fitting recessed part is formed as a stepped recess and the fitting projected part is formed as a stepped projection that fits the stepped recess with a sealing face formed as an abutting face by a stepped part of the fitting recessed part and a stepped part of the fitting projected part abutting each other.

18. The inline concentration measurement device of claim 12, wherein
the light incident part includes a collimator lens for collimating incident light entering to the gas flow path part for the optical path.

19. The inline concentration measurement device of claim 12, wherein
the window members are configured to obliquely cross the optical path of the gas flow path part for the optical path.

20. The inline concentration measurement device of claim 12, wherein
a gas inflow path communicating with the first communication part for sending gas thereto is provided and a cross section area of the gas inflow path is larger than a cross section area of the flow path in the first communication part.

21. The inline concentration measurement device of claim 12, wherein
the measurement cell main body includes a block body, an end portion of which is configured to support the window member of the light receiving part, and
the second communication part is formed in the block body.

* * * * *